United States Patent [19]
Tomita et al.

[11] Patent Number: 5,304,633
[45] Date of Patent: Apr. 19, 1994

[54] FRAGMENTS OF LACTOFERRIN HAVING POTENT ANTIMICROBIAL ACTIVITY

[75] Inventors: Mamoru Tomita, Kanagawa; Kohzo Kawase; Mitsunori Takase, both of Saitama; Wayne R. Bellamy, Kanagawa; Kohji Yamauchi, Kanagawa; Hiroyuki Wakabayashi, Kanagawa, all of Japan

[73] Assignee: Morinaga Milk Industry Co., Ltd., Tokyo, Japan

[21] Appl. No.: 755,161

[22] Filed: Sep. 5, 1991

[30] Foreign Application Priority Data

Sep. 7, 1990 [JP] Japan .................................. 2-238364
Jul. 25, 1991 [JP] Japan .................................. 3-186260

[51] Int. Cl.$^5$ ...................... A61K 37/02; C07K 5/12; C07K 7/10; C07K 7/08
[52] U.S. Cl. .................................. 530/326; 530/317; 530/324; 514/13
[58] Field of Search ...................... 530/326, 317, 324; 514/13, 11, 12

[56] References Cited

PUBLICATIONS

Metz-Boutigue, *Febs Letters,* vol. 142, No. 1, 107-10, Jun. 1982.
Goodman, et al, *Biochemical and Biophysical Research Communications,* vol. 180, No. 1, 75-84, 1991.
Pentecost et al, *J. Biol. Chem.,* vol. 262, No. 21, 1034-39, 1987.
Metz-Boutigue et al, *Eur. J. Biochem,* vol. 145, 659-676, 1984.

*Primary Examiner*—Merrell C. Cashion, Jr.
*Assistant Examiner*—S. G. Marshall
*Attorney, Agent, or Firm*—Wenderoth, Lind & Ponack

[57] ABSTRACT

An antimicrobial peptide containing at least the following amino acid sequence (a), (b), (c) or (d), an antimicrobial agent containing the said antimicrobial peptide as active components at a concentration of at least 5 ppm (weight), an antimicrobial composition the said antimicrobial peptide and a method for processing products which uses the antimicrobial agent containing the said antimicrobial peptide.

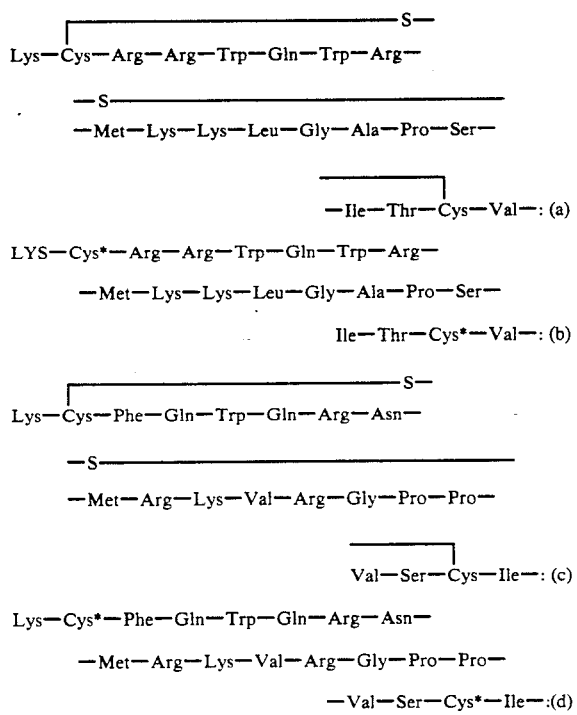

(the Cys* appearing herein represents cysteine in which the thiol group has been chemically modified in order to prevent disulfide bond formation)

7 Claims, 2 Drawing Sheets

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
      ( A ) LENGTH: 20 amino acids
      ( B ) TYPE: amino acid
      ( C ) STRANDEDNESS: single
      ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
      ( A ) ORGANISM:
      ( B ) STRAIN:
      ( C ) INDIVIDUAL ISOLATE:
      ( D ) DEVELOPMENTAL STAGE:
      ( E ) HAPLOTYPE:
      ( F ) TISSUE TYPE:
      ( G ) CELL TYPE:
      ( H ) CELL LINE:
      ( I ) ORGANELLE:

( v i i ) IMMEDIATE SOURCE:
      ( A ) LIBRARY:
      ( B ) CLONE:

( v i i i ) POSITION IN GENOME:
      ( A ) CHROMOSOME/SEGMENT:
      ( B ) MAP POSITION:
      ( C ) UNITS:

( i x ) FEATURE:
      ( A ) NAME/KEY: modified site
      ( B ) LOCATION: 2
      ( C ) IDENTIFICATION METHOD:
      ( D ) OTHER INFORMATION: /note="thiol group of Cys residue at location 2 connected by disulfide bond with thiol group of Cys residue at location 19"

( i x ) FEATURE:
      ( A ) NAME/KEY: modified site
      ( B ) LOCATION: 19
      ( C ) IDENTIFICATION METHOD:
      ( D ) OTHER INFORMATION: /note="thiol group of Cys residue at location 19 connected by disulfide bond with thiol group of Cys residue at location 2"

( x ) PUBLICATION INFORMATION:
      ( A ) AUTHORS:
      ( B ) TITLE:
      ( C ) JOURNAL:
      ( D ) VOLUME:
      ( E ) ISSUE:
      ( F ) PAGES:
      ( G ) DATE:
      ( H ) DOCUMENT NUMBER:
      ( I ) FILING DATE:
      ( J ) PUBLICATION DATE:
      ( K ) RELEVANT RESIDUES IN SEQ ID NO:

( x i ) SEQUENCE DESCRIPTION: SEQ ID NO:1:

Lys Cys Arg Arg Trp Gln Trp Arg Met Lys Lys Leu Gly Ala Pro

Ser Ile Thr Cys Val
                 20

(2) INFORMATION FOR SEQ ID NO:2:

(i) SEQUENCE CHARACTERISTICS:
        (A) LENGTH: 20 amino acids
        (B) TYPE: amino acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:
        (A) NAME/KEY: modified site
        (B) LOCATION: 2
        (C) IDENTIFICATION METHOD:
        (D) OTHER INFORMATION: /note="Cys residue
            having thiol group chemically modified to prevent
            disulfide bond formation"

(ix) FEATURE:
        (A) NAME/KEY: modified site
        (B) LOCATION: 19
        (C) IDENTIFICATION METHOD:
        (D) OTHER INFORMATION: /note="Cys residue
            having thiol group chemically modified to prevent
            disulfide bond formation"

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (H) DOCUMENT NUMBER:
        (I) FILING DATE:
        (J) PUBLICATION DATE:
        (K) RELEVANT RESIDUES IN SEQ ID NO:

(xi) SEQUENCE DESCRIPTION: SEQ ID NO:2:

Lys Xaa Arg Arg Trp Gln Trp Arg Met Lys Lys Leu Gly Ala Pro
 1               5                  10                   15

Ser Ile Thr Xaa Val
                 20

(2) INFORMATION FOR SEQ ID NO:3:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY: modified site
    (B) LOCATION: 2
    (C) IDENTIFICATION METHOD:
    (D) OTHER INFORMATION: /note="thiol group of
        Cys residue at location 2 connected by disulfide bond
        with thiol group of Cys residue at location 19"

(ix) FEATURE:
    (A) NAME/KEY: modified site
    (B) LOCATION: 19
    (C) IDENTIFICATION METHOD:
    (D) OTHER INFORMATION: /note="thiol group of
        Cys residue at location 19 connected by disulfide bond
        with thiol group of Cys residue at location 2"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:3:

Lys Cys Phe Gln Trp Gln Arg Asn Met Arg Lys Val Arg Gly Pro
1               5                   10                  15

Pro Val Ser Cys Ile
            20

(2) INFORMATION FOR SEQ ID NO:4:

(i) SEQUENCE CHARACTERISTICS:
    (A) LENGTH: 20 amino acids
    (B) TYPE: amino acid
    (C) STRANDEDNESS: single
    (D) TOPOLOGY: linear (ii) MOLECULE TYPE:

( i i i ) HYPOTHETICAL:

( i v ) ANTI-SENSE:

( v ) FRAGMENT TYPE:

( v i ) ORIGINAL SOURCE:
    ( A ) ORGANISM:
    ( B ) STRAIN:
    ( C ) INDIVIDUAL ISOLATE:
    ( D ) DEVELOPMENTAL STAGE:
    ( E ) HAPLOTYPE:
    ( F ) TISSUE TYPE:
    ( G ) CELL TYPE:
    ( H ) CELL LINE:
    ( I ) ORGANELLE:

( v i i ) IMMEDIATE SOURCE:
    ( A ) LIBRARY:
    ( B ) CLONE:

( v i i i ) POSITION IN GENOME:
    ( A ) CHROMOSOME/SEGMENT:
    ( B ) MAP POSITION:
    ( C ) UNITS:

( i x ) FEATURE:
    ( A ) NAME/KEY: modified site
    ( B ) LOCATION: 2
    ( C ) IDENTIFICATION METHOD:
    ( D ) OTHER INFORMATION: /note="Cys residue
        having thiol group chemically modified to prevent
        disulfide bond formation"

( i x ) FEATURE:
    ( A ) NAME/KEY: modified site
    ( B ) LOCATION: 19
    ( C ) IDENTIFICATION METHOD:
    ( D ) OTHER INFORMATION: /note="Cys residue
        having thiol group chemically modified to prevent
        disulfide bond formation"

( x ) PUBLICATION INFORMATION:
    ( A ) AUTHORS:
    ( B ) TITLE:
    ( C ) JOURNAL:
    ( D ) VOLUME:
    ( E ) ISSUE:
    ( F ) PAGES:
    ( G ) DATE:
    ( H ) DOCUMENT NUMBER:
    ( I ) FILING DATE:
    ( J ) PUBLICATION DATE:
    ( K ) RELEVANT RESIDUES IN SEQ ID NO:

( x i ) SEQUENCE DESCRIPTION: SEQ ID NO:4:

Lys Xaa Phe Gln Trp Gln Arg Asn Met Arg Lys Val Arg Gly Pro
1                5                    10                    15

Pro Val Ser Xaa Ile
                20

( 2 ) INFORMATION FOR SEQ ID NO:5:

( i ) SEQUENCE CHARACTERISTICS:
        ( A ) LENGTH: 25 amino acids
        ( B ) TYPE: amino acid
        ( C ) STRANDEDNESS: single
        ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
        ( A ) ORGANISM:

( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:
                    ( B ) MAP POSITION:
                    ( C ) UNITS:

( i x ) FEATURE:
                    ( A ) NAME/KEY: modified site
                    ( B ) LOCATION: 3
                    ( C ) IDENTIFICATION METHOD:
                    ( D ) OTHER INFORMATION: /note="thiol group of
                        Cys residue at location 3 connected by disulfide bond
                        with thiol group of Cys residue at location 20"

( i x ) FEATURE:
                    ( A ) NAME/KEY: modified site
                    ( B ) LOCATION: 20
                    ( C ) IDENTIFICATION METHOD:
                    ( D ) OTHER INFORMATION: /note="thiol group of
                        Cys residue at location 20 connected by disulfide bond
                        with thiol group of Cys residue at location 3"

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:5:

Phe Lys Cys Arg Arg Trp Gln Trp Arg Met Lys Lys Leu Gly Ala
1               5                   10                  15

Pro Ser Ile Thr Cys Val Arg Arg Ala Phe
                20                  25

( 2 ) INFORMATION FOR SEQ ID NO:6:

( i ) SEQUENCE CHARACTERISTICS:
                    ( A ) LENGTH: 38 amino acids
                    ( B ) TYPE: amino acid
                    ( C ) STRANDEDNESS: single
                    ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
        ( A ) LIBRARY:
        ( B ) CLONE:

( v i i i ) POSITION IN GENOME:
        ( A ) CHROMOSOME/SEGMENT:
        ( B ) MAP POSITION:
        ( C ) UNITS:

( i x ) FEATURE:
        ( A ) NAME/KEY: modified site
        ( B ) LOCATION: 16
        ( C ) IDENTIFICATION METHOD:
        ( D ) OTHER INFORMATION: /note="thiol group of
            Cys residue at location 16 connected by disulfide bond
            with thiol group of Cys residue at location 33"

( i x ) FEATURE:
        ( A ) NAME/KEY: modified site
        ( B ) LOCATION: 33
        ( C ) IDENTIFICATION METHOD:
        ( D ) OTHER INFORMATION: /note="thiol group of
            Cys residue at location 33 connected by disulfide bond
            with thiol group of Cys residue at location 16"

( x ) PUBLICATION INFORMATION:
        ( A ) AUTHORS:
        ( B ) TITLE:
        ( C ) JOURNAL:
        ( D ) VOLUME:
        ( E ) ISSUE:
        ( F ) PAGES:
        ( G ) DATE:
        ( H ) DOCUMENT NUMBER:
        ( I ) FILING DATE:
        ( J ) PUBLICATION DATE:
        ( K ) RELEVANT RESIDUES IN SEQ ID NO:

( x i ) SEQUENCE DESCRIPTION: SEQ ID NO:6:

```
Lys Asn Val Arg Trp Cys Thr Ile Ser Gln Pro Glu Trp Phe Lys
 1               5                  10                   15

Cys Arg Arg Trp Gln Trp Arg Met Lys Lys Leu Gly Ala Pro Ser
                20                  25                   30

Ile Thr Cys Val Arg Arg Ala Phe
                35
```

( 2 ) INFORMATION FOR SEQ ID NO:7:

( i ) SEQUENCE CHARACTERISTICS:
            ( A ) LENGTH: 32 amino acids
            ( B ) TYPE: amino acid
            ( C ) STRANDEDNESS: single
            ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
            ( A ) ORGANISM:
            ( B ) STRAIN:
            ( C ) INDIVIDUAL ISOLATE:
            ( D ) DEVELOPMENTAL STAGE:
            ( E ) HAPLOTYPE:
            ( F ) TISSUE TYPE:
            ( G ) CELL TYPE:
            ( H ) CELL LINE:
            ( I ) ORGANELLE:

( v i i ) IMMEDIATE SOURCE:
            ( A ) LIBRARY:
            ( B ) CLONE:

(viii) POSITION IN GENOME:
    (A) CHROMOSOME/SEGMENT:
    (B) MAP POSITION:
    (C) UNITS:

(ix) FEATURE:
    (A) NAME/KEY: modified site
    (B) LOCATION: 10
    (C) IDENTIFICATION METHOD:
    (D) OTHER INFORMATION: /note="thiol group of
        Cys residue at location 10 connected by disulfide bond
        with thiol group of Cys residue at location 27"

(ix) FEATURE:
    (A) NAME/KEY: modified site
    (B) LOCATION: 27
    (C) IDENTIFICATION METHOD:
    (D) OTHER INFORMATION: /note="thiol group of
        Cys residue at location 27 connected by disulfide bond
        with thiol group of Cys residue at location 10"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:7:

```
Thr Ile Ser Gln Pro Glu Trp Phe Lys Cys Arg Arg Trp Gln Trp
  1               5                  10                  15
Arg Met Lys Lys Leu Gly Ala Pro Ser Ile Thr Cys Val Arg Arg
                 20                  25                  30
Ala Phe
```

(2) INFORMATION FOR SEQ ID NO:8:

(i) SEQUENCE CHARACTERISTICS:
        (A) LENGTH: 36 amino acids
        (B) TYPE: amino acid
        (C) STRANDEDNESS: single
        (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
        (A) ORGANISM:
        (B) STRAIN:
        (C) INDIVIDUAL ISOLATE:
        (D) DEVELOPMENTAL STAGE:
        (E) HAPLOTYPE:
        (F) TISSUE TYPE:
        (G) CELL TYPE:
        (H) CELL LINE:
        (I) ORGANELLE:

(vii) IMMEDIATE SOURCE:
        (A) LIBRARY:
        (B) CLONE:

(viii) POSITION IN GENOME:
        (A) CHROMOSOME/SEGMENT:
        (B) MAP POSITION:
        (C) UNITS:

(ix) FEATURE:

( A ) NAME/KEY: modified site
                    ( B ) LOCATION: 9
                    ( C ) IDENTIFICATION METHOD:
                    ( D ) OTHER INFORMATION: /note="thiol group of
                        Cys residue at location 9 connected by disulfide bond
                        with thiol group of Cys residue at location 26"

( i x ) FEATURE:
                    ( A ) NAME/KEY: modified site
                    ( B ) LOCATION: 26
                    ( C ) IDENTIFICATION METHOD:
                    ( D ) OTHER INFORMATION: /note="thiol group of
                        Cys residue at location 26 connected by disulfide bond
                        with thiol group of Cys residue at location 9"

( i x ) FEATURE:
                    ( A ) NAME/KEY: modified site
                    ( B ) LOCATION: 35
                    ( C ) IDENTIFICATION METHOD:
                    ( D ) OTHER INFORMATION: /note="thiol group of
                        Cys residue at location 35 connected by disulfide bond
                        with thiol group of Cys residue at location 10 of
                        SEQ ID NO. 9"

( x ) PUBLICATION INFORMATION:
                    ( A ) AUTHORS:
                    ( B ) TITLE:
                    ( C ) JOURNAL:
                    ( D ) VOLUME:
                    ( E ) ISSUE:
                    ( F ) PAGES:
                    ( G ) DATE:
                    ( H ) DOCUMENT NUMBER:
                    ( I ) FILING DATE:
                    ( J ) PUBLICATION DATE:
                    ( K ) RELEVANT RESIDUES IN SEQ ID NO:

( x i ) SEQUENCE DESCRIPTION: SEQ ID NO:8:

Val  Ser  Gln  Pro  Glu  Ala  Thr  Lys  Cys  Phe  Gln  Trp  Gln  Arg  Asn
1                   5                        10                        15

Met  Arg  Lys  Val  Arg  Gly  Pro  Pro  Val  Ser  Cys  Ile  Lys  Arg  Asp
                    20                       25                        30

Ser  Pro  Ile  Gln  Cys  Ile
                    35

( 2 ) INFORMATION FOR SEQ ID NO:9:

( i ) SEQUENCE CHARACTERISTICS:
                    ( A ) LENGTH: 11 amino acids
                    ( B ) TYPE: amino acid
                    ( C ) STRANDEDNESS: single
                    ( D ) TOPOLOGY: linear ( i i ) MOLECULE TYPE:

( i i i ) HYPOTHETICAL:

( i v ) ANTI-SENSE:

( v ) FRAGMENT TYPE:

( v i ) ORIGINAL SOURCE:
                    ( A ) ORGANISM:
                    ( B ) STRAIN:
                    ( C ) INDIVIDUAL ISOLATE:
                    ( D ) DEVELOPMENTAL STAGE:
                    ( E ) HAPLOTYPE:
                    ( F ) TISSUE TYPE:
                    ( G ) CELL TYPE:
                    ( H ) CELL LINE:
                    ( I ) ORGANELLE:

( v i i ) IMMEDIATE SOURCE:
                    ( A ) LIBRARY:
                    ( B ) CLONE:

( v i i i ) POSITION IN GENOME:
                    ( A ) CHROMOSOME/SEGMENT:

(B) MAP POSITION:
(C) UNITS:

(ix) FEATURE:
    (A) NAME/KEY: modified site
    (B) LOCATION: 10
    (C) IDENTIFICATION METHOD:
    (D) OTHER INFORMATION: /note="thiol group of
        Cys residue at location 10 connected by disulfide bond
        with thiol group of Cys residue at location 35 of
        SEQ ID NO. 8"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:9:

```
Gly  Arg  Arg  Arg  Arg  Ser  Val  Gln  Trp  Cys  Ala
 1                  5                        10
```

(2) INFORMATION FOR SEQ ID NO:10:

(i) SEQUENCE CHARACTERISTICS:
    (A) LENGTH: 25 amino acids
    (B) TYPE: amino acid
    (C) STRANDEDNESS: single
    (D) TOPOLOGY: linear (ii) MOLECULE TYPE:

(iii) HYPOTHETICAL:

(iv) ANTI-SENSE:

(v) FRAGMENT TYPE:

(vi) ORIGINAL SOURCE:
    (A) ORGANISM:
    (B) STRAIN:
    (C) INDIVIDUAL ISOLATE:
    (D) DEVELOPMENTAL STAGE:
    (E) HAPLOTYPE:
    (F) TISSUE TYPE:
    (G) CELL TYPE:
    (H) CELL LINE:
    (I) ORGANELLE:

(vii) IMMEDIATE SOURCE:
    (A) LIBRARY:
    (B) CLONE:

(viii) POSITION IN GENOME:
    (A) CHROMOSOME/SEGMENT:
    (B) MAP POSITION:
    (C) UNITS:

(ix) FEATURE:
    (A) NAME/KEY: modified site
    (B) LOCATION: 4
    (C) IDENTIFICATION METHOD:
    (D) OTHER INFORMATION: /note="thiol group of
        Cys residue at location 4 connected by disulfide bond
        with thiol group of Cys residue at location 21"

(ix) FEATURE:
    (A) NAME/KEY: modified site
    (B) LOCATION: 21
    (C) IDENTIFICATION METHOD:
    (D) OTHER INFORMATION: /note="thiol group of
        Cys residue at location 21 connected by disulfide bond
        with thiol group of Cys residue at location 4"

(x) PUBLICATION INFORMATION:
    (A) AUTHORS:
    (B) TITLE:
    (C) JOURNAL:
    (D) VOLUME:
    (E) ISSUE:
    (F) PAGES:
    (G) DATE:
    (H) DOCUMENT NUMBER:
    (I) FILING DATE:
    (J) PUBLICATION DATE:
    (K) RELEVANT RESIDUES IN SEQ ID NO:

(xi) SEQUENCE DESCRIPTION: SEQ ID NO:10:

Ala Thr Lys Cys Phe Gln Trp Gln Arg Asn Met Arg Lys Val Arg
 1           5                   10                  15

Gly Pro Pro Val Ser Cys Ile Lys Arg Asp
                20              25

FRAGMENTS OF LACTOFERRIN HAVING POTENT ANTIMICROBIAL ACTIVITY

BACKGROUND OF THE INVENTION

1. Field of the Invention

The present invention concerns antimicrobial peptides and an antimicrobial agent. More specifically, it concerns an antimicrobial agent containing novel antimicrobial peptides, salts of these peptides, or a mixture thereof, as active components, a method for treating products which uses this antimicrobial agent, and an antimicrobial peptide compound containing an antimicrobial peptide, a salt of this peptide or a mixture of at least two of these salts, as active components.

In the specification of the present invention, the amino acids and peptides are represented by the abbreviations employed by IUPAC-IUB Committee on Biochemical Nomenclature, such as the following abbreviations.

Ala-: L-Alanine residue
Arg-: L-Arginine residue
Asn-: L-Asparagine residue
Asp-: L-Aspartic acid residue
Cys-: L-Cysteine residue
Gln-: L-Glutamine residue
Glu-: L-Glutamic acid residue
Gly-: L-Glycine residue
His-: L-Histidine residue
Ile-: L-Isoleucine residue
Leu-: L-Leucine residue
Lys-: L-Lysine residue
Mct-: L-Methionine residue
Phe-: L-Phenylalanine residue
Pro-: L-Proline residue
Ser-: L-Serine residue
Thr-: L-Threonine residue
Trp-: L-Tryptophan residue
Tyr-: L-Tyrosine residue
Val-: L-Valine residue.

2. Description of Related Prior Art

Numerous inventions concerning peptides which possess antimicrobial properties against various microorganisms have so far been reported. Examples include a phosphonotripeptide (Japanese Patent Provisional Publication No. 106689/82), a phosphonodipeptide derivative (Japanese Patent Provisional Publication No. 13594/83) and a cyclic peptide derivative (Japanese Patent Provisional Publication No. 213744/83) effective against gram-positive and gram-negative bacteria, a peptide demonstrating an antimicrobial and antiviral action (Japanese Patent Provisional Publication No. 51247/84), a polypeptide effective against yeast (Japanese Patent Provisional Publication No. 130599/85), a saccharopeptide derivative effective against gram-positive bacteria (Japanese Patent Provisional Publication No. 172998/85, Japanese Patent Provisional Publication No. 251699/86, Japanese Patent Provisional Publication No. 44598/88), an oligopeptide effective against gram-positive bacteria (Japanese Patent Provisional Publication No. 22798/87), a peptidal antibiotic substance (Japanese Patent Provisional Publication No. 51697/87, Japanese Patent Provisional Publication No. 17897/88) as well as an antimicrobial peptide extracted from blood cells of North American king crabs (Japanese Patent Provisional Publication No. 53799/90) and an antimicrobial peptide isolated from blood lymph of honeybees (Japanese Patent Provisional Publication No. 500084/90).

On the other hand, lactoferrin, which is a natural iron-binding protein contained in tears, saliva, peripheral blood, milk etc. is known to demonstrate an antimicrobial activity against *Escherichia coli*, Candida, Clostridium, and other harmful microorganisms (Journal of Pediatrics, Vol. 94, p. 1, 1979).

The inventors of the present invention, in planning to cheaply isolate from nature a substance which possesses strong antimicrobial properties, which has no undesirable side effects (such as antigenicity) and is heat-resistant, focused on whey, a by-product of cheese manufacturing, and conducted research regarding the antimicrobial properties of the lactoferrin contained in it. They discovered that the catabolite of lactoferrin hydrolysis by an acid or an enzyme has stronger heat resistant and antimicrobial properties than the non-hydrolyzed lactoferrin, and have filed a patent application (Japanese Patent Application No. 13315/90). The composition and action of the antimicrobial substance present in such a lactoferrin hydrolysate have not been sufficiently understood, however, and therefore, the development of an effective antimicrobial agent had not yet been achieved.

SUMMARY OF THE INVENTION

The objective of the present invention is to provide novel antimicrobial peptides which can be isolated from lactoferrin hydrolysate and contain specific amino acid sequences, an antimicrobial agent containing this peptide as an active component, a method for treating products which uses this antimicrobial agent, and an antimicrobial composition containing this peptide as an active component.

The present invention provides (1) an antimicrobial peptide containing at least the following amino acid sequence (a), (b), (c) or (d), (2) an antimicrobial agent characterized by the fact that it contains substances selected from the group consisting of peptides containing at least the following amino acid sequences, and pharmaceutically or sitologically approved salts thereof, or a mixture of at least two of the above, as active components, (3) a method for treating products which uses this antimicrobial agent, and (4) a peptide compound which is characterized by the fact that it contains substances selected from the group consisting of peptides containing at least the following amino acid sequences, and pharmaceutically or sitologically approved salts thereof, or a mixture of at least two of the above, as active components.

Lys—Cys—Arg—Arg—Trp—Gln—Trp—Arg—Met—Lys—Lys—Leu—Gly—Ala—Pro—Ser—
Ile—Thr—Cys—Val—: (a) (SEQ ID NO. 1)

(with disulfide bond S—S between the two Cys residues)

-continued

Lys—Cys*—Arg—Arg—Trp—Gln—Trp—Arg—Met—Lys—Lys—Leu—Gly—Ala—Pro—Ser—

Ile—Thr—Cys*—Val: (b) (SEQ ID NO. 2)

```
          ┌─────────────S────────S─────────────────────
Lys—Cys—Phe—Gln—Trp—Gln—Arg—Asn—Met—Arg—Lys—Val—Arg—Gly—Pro—Pro—
```

Val—Ser—Cys—Ile—: (c) (SEQ ID NO. 3)

or

Lys—Cys*—Phe—Gln—Trp—Gln—Arg—Asn—Met—Arg—Lys—Val—Arg—Gly—Pro—Pro—

Val—Ser—Cys*—Ile—: (d) (SEQ ID NO. 4)

(the Cys* appearing herein represents cysteine in which the thiol group has been chemically modified in order to prevent disulfide bond formation)

BRIEF DESCRIPTION OF THE DRAWINGS

Both

DETAILED DESCRIPTION OF THE INVENTION

Figure 1:
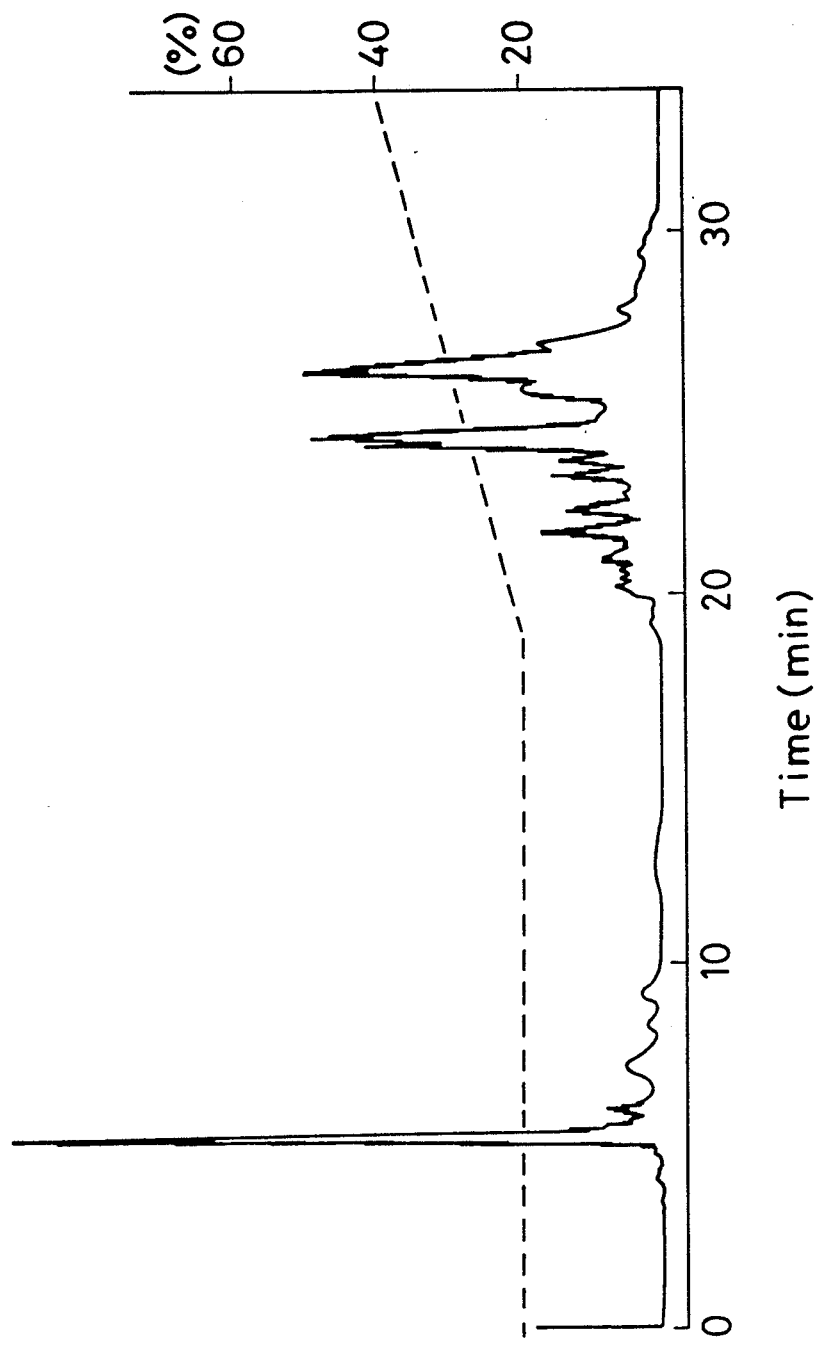
FIG. 1 and FIG. 2 show elution curves of the antimicrobial peptides obtained by high-performance liquid chromatography.

The peptides of the present invention can be chemically synthesized by conventional methods, but can also be isolated, for example, from lactoferrin of mammals in the following manner.

That is, the peptides can be isolated from a hydrolysate (this hydrolysate will be referred to hereinafter as "LF hydrolysate") obtained from, for example, acid or enzymatic hydrolysis of lactoferrin, apolactoferrin (which is lactoferrin from which iron has been removed) or metal-saturated lactoferrin (which is apolactoferrin which has formed a chelate with a metal such as iron, copper, zinc, manganese, etc.), etc. (hereinafter collectively referred to as "LF"), which have been isolated by conventional methods, such as ion-exchange chromatography, etc., from colostrum, transitional milk, normal milk, late lactation milk, etc., of mammals (such as human, cow, water buffalo, horse, goat or sheep), and the processed products thereof, such as skimmed milk, whey, etc. (hereinafter referred to as "milk, etc.").

In cases in which the LF hydrolysate is obtained using an acid, the LF is dissolved in water, purified water etc. at a concentration of 0.1 to 20% (weight, the same hereinafter unless otherwise indicated), preferably 5 to 15%, after which an inorganic acid such as hydrochloric acid or phosphoric acid, or an organic acid such as citric acid, is added to the solution and the pH of the solution is adjusted to 1 to 4. The LF is hydrolyzed by heating the resultant pH-adjusted solution for a prescribed time-period to an appropriate temperature. For example, if the pH was adjusted to 1 to 2, the solution is heated to 80° to 130° C., and if the pH was adjusted to 2 to 4, it is heated to 100° to 130° C., for 1 to 120 minutes in each case. Next, the reaction solution is cooled in by conventional methods and neutralized, desalted or decolorized, as needed.

In the cases in which the LF hydrolysate is obtained using an enzyme, the LF is dissolved in water, sterilized water, purified water etc. to a concentration of 0.5 to 20%, preferably 5 to 15%, the enzyme is added to it and hydrolysis is carried out. There are no particular limitations on the enzyme used, and commercially available products such as Molsin F (trademark; manufactured by Seishin Pharmaceutical Co.; optimal pH 2.5 to 3.0), porcine pepsin (manufactured by Wako Pure Chemical Industries; optimal pH 2 to 3), Sumizyme AP (trademark; manufactured by New Japan Chemical Co.,; optimal pH 3.0), Amano A (trademark; manufactured by Amano Pharmaccutical Co.; optimal pH 7.0), trypsin (manufactured by Novo Co; optimal pH 8.0) and other endopeptidases can be used individually or in any desired combination. In addition, exopeptidase derived from, for example, lactobacilli, obtained according to the method cited in Japanese Patent Publication No. 43878/73, or commercially available peptidases employed in the production of soy sauce (manufactured by Tanabe Pharmaceutical Co.), etc., can be used in combination with these enzymes. The quantity of enzyme used should be within a range of 0.1 to 5.0% with respect to the substrate.

Hydrolysis of LF is performed by adjusting the pH of the LF solution approximately to the optimal pH of the enzyme used, adding the enzyme and maintaining the solution at 15° to 55° C., preferably 30° to 50° C., for 30 to 600 minutes, preferably for 60 to 300 minutes. Next, the reaction solution is maintained as it is or neutralized, the enzyme is inactivated by heating using conventional methods and neutralization or decoloration can be performed, as needed.

By using conventional chromatographic methods etc., the antimicrobial peptides of the present invention can be isolated from the LF hydrolysate so obtained. For example, the peptides can be isolated in high-performance liquid chromatography in which TSK gel ODS 120 T (manufactured by Tosoh Co.) is used by eluting a fixed fraction in an acetonitrile gradient.

By following the above method, the antimicrobial peptides of the present invention can be isolated from an LF hydrolysate. As shown in Experiments 2, 4, 6 and 8, the isolated antimicrobial peptides contain, in every case, the amino acid sequence A or B, and changes in the amino acid sequences in sections other than these common amino acid sequences were found to have no effect on the antimicrobial properties (see Experiments 1, 3, 5 and 7).

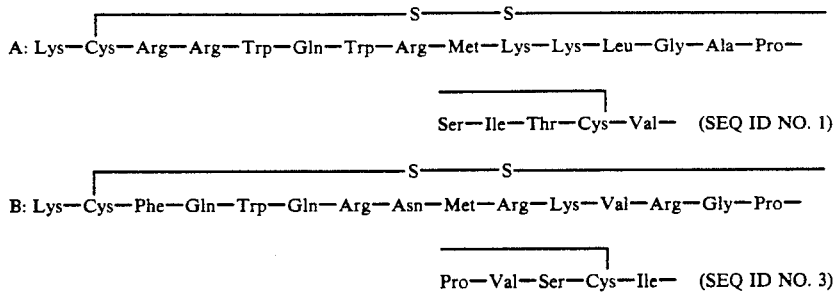

(SEQ ID NO. 1)

(SEQ ID NO. 3)

Examples of chemical synthesis of the antimicrobial peptides of the present invention are as follows. Using an automated peptide synthesizer (such as the one manufactured by Pharmacia LKB Biotechnology Co., LKB Biolynk 4170), the peptides are synthesized following the solid-phase peptide synthesis method of Sheppard el al. (Journal of Chemical Society Perkin I, p. 538, 1981). N,N'-dicyclohexylcarbodiimide is added to amino acids whose amine functional groups are protected by 9-fluorenylmethoxycarbonyl (Fmoc) groups (hereinafter referred to as "Fmoc-amino acid") and anhydrides of the desired amino acids are produced, and these Fmoc-amino acid anhydrides are used for synthesis. In order to produce a peptide chain, an Fmoc-amino acid anhydride corresponding to the C-terminal amino acid residue is fixed to Ultrosyn A resin (manufactured by Pharmacia LKB Biotechnology Co.) through the carboxyl group thereof, using dimethylaminopyridine as a catalyst. Next, the resin is washed with dimethylformamide containing piperidine, and the protecting group of the amine functional group of the C-terminal amino acid is removed. Next, an Fmoc-amino acid anhydride corresponding to the amino acid residue which is second from the C-terminal of the amino acid sequence of the desired peptide is coupled to the unprotected amine functional group of the first amino acid fixed to the resin through the above-mentioned C-terminal amino acid residue. Subsequently the successive desired amino acids are fixed in the same manner. In the case of cysteine, however, an Fmoc-amino acid whose SH group was protected by acetoamidomethyl is used. After coupling of all the amino acids is completed and the peptide chain of the desired amino acid sequence is formed, the protective groups other than acetoamidomethyl are removed and the peptide is released with a solvent (composed of, for example, 94% trifluoroacetic acid, 5% phenol and 1% ethandiol), and the acetoamidomethylated peptide is purified using high-performance liquid chromatography. Next, the acetoamidomethylated peptide is dissolved in 90% acetic acid aqueous solution at a concentration of 0.5 mM, to which is added ⅛ volume of 1M hydrochloric acid and eight volumes of a 90% acetic acid aqueous solution containing 50 mM iodine and the solution is vigorously stirred for 30 minutes. Next, 1/22.5 volumes of 1M sodium thiosulfate aqueous solution is added and the reaction is stopped, and the solution is concentrated to ⅛ of its volume. This concentrated solution is fractionated with Sephadex G-15 (manufactured by Pharmacia Co.) and a peptide which has formed SS bonds is purified.

The peptides synthesized in this manner posses antimicrobial properties similar to that of the peptides isolated from nature, as shown in Experiment 9.

The following peptides whose thiol groups have been chemically modified using a conventional method (for example, by pyridylethylation) in order to prevent formation of disulfide bonds of the antimicrobial peptides obtained by enzymatic hydrolysis or the antimicrobial peptides obtained by synthesis, similarly possesses antimicrobial properties (Experiment 11).

Lys—Cys*—Arg—Arg—Trp—Gln—Trp—Arg—Met—Lys—Lys—Leu—Gly—Ala—Pro—

Ser—Ile—Thr—Cys*—Val— (SEQ ID NO. 2)

and

Lys—Cys*—Phe—Gln—Trp—Gln—Arg—Asn—Met—Arg—Lys—Val—Arg—Gly—Pro—

Pro—Val—Ser—Cys*—Ile— (SEQ ID NO. 4)

(the Cys* in the above-mentioned amino acid sequence represents cysteine whose thiol group has been chemically modified)

The antimicrobial peptides so obtained, the pharmaceutically or sitologically approved salts thereof, or a mixture of at least two of the above, are included as active components at a concentration of at least 5 ppm and preferably 10 to 50 ppm, in order to obtain the antimicrobial agent or the antimicrobial peptide compound of the present invention.

The antimicrobial peptides of the present invention or their derivatives can be administered to humans or to animals without further modifications, can be used in food products (such as chewing gum), medicinal pharmaceutical products (such as eye medications, mastitis medications, diarrhea medications and athlete's foot medications), non-medicinal pharmaceutical products (such as mouth washes, antiperspirants and hair tonics), various cosmetic products (such as hair conditioners, creams and lotions), various tooth-brushing products (such as toothpastes and toothbrushes), various feminine hygiene products, various baby products (such as diapers), various geriatric products (such as denture cement and diapers), various cleaning agents (such as soaps, medicinal soaps, shampoos, rinses, laundry detergents, kitchen detergents and house detergents), various sterilized products (such as sterilized kitchen paper and sterilized toilet paper), feed (such as pet feed) and materials which serve as raw materials of the above, they can also be added to, compounded with, sprayed onto, adhered to or used for coating or impregnation of any and all products wherein prevention or inhibition of microbial proliferation is generally desired or otherwise used for treating any and all products wherein prevention or inhibition of microbial proliferation is generally desired.

The antimicrobial peptides of the present invention or their derivatives can be used concomitantly with other antimicrobial agents, administered to humans or to animals without further modifications or used in food products (such as chewing gums), medicinal pharmaceutical products (such as eye medications, mastitis medications, diarrhea medications and athlete's foot medications), non-medicinal pharmaceutical products (such as mouth washes, antiperspirants and hair tonics), various cosmetic products (such as hair conditioners, creams and lotions), various tooth-brushing products (such as toothpastes and toothbrushes), various feminine hygiene products, various baby products (such as diapers), various geriatric products (such as denture cement and diapers), various cleaning agents (such as soaps, medicinal soaps, shampoos, rinses, laundry detergents, kitchen detergents and house detergents), various sterilized products (such as sterilized kitchen paper and sterilized toilet paper), feed (such as pet feed) and materials which serve as raw materials of the above, they can also be added to, compounded with, sprayed onto, adhered to or used for coating or impregnation of any and all products wherein prevention or inhibition of microbial proliferation is generally desired or otherwise used for treating any and all products wherein prevention or inhibition of microbial proliferation is generally desired.

Next, the present invention will be described in detail by means of Experiments.

EXPERIMENT 1

This experiment was performed in order to study the antimicrobial activity of an antimicrobial peptide isolated from an enzymatic hydrolysate of bovine LF.

(1) Experimental method

1. Preparation of a pre-incubation solution

One platinum loop was collected from a stock slant of *Escherichia coli*, streaked on a standard agar medium (manufactured by Nissui Pharmaceutical Co.) and incubated under aerobic conditions for 16 hours at 35° C., the colonies which grew on the surface of the standard agar medium were collected using a platinum loop, suspended in sterilized physiological saline solution, the turbidity was measured using a spectrophotometer (manufactured by Hitachi Manufacturing Co.) and adjusted to 1.0 (measured wavelength 660 nm) and a pre-incubation solution was prepared.

2. Preparation of a basal medium

Bactocasitone (manufactured by Difco Laboratory Co.) was dissolved at a concentration of 1% in purified water, the pH was adjusted to 7.0 with 1M sodium hydroxide, the solution was sterilized at 115° C. for 15 minutes and a basal medium (liquid medium) was prepared.

3. Preparation of the test media and of the control medium

Each sample was dissolved at a concentration of 0.01% in purified water, sterilization was performed by using a sterilization filter (manufactured by Advantek Co.) and test media, prepared by adding samples at concentrations of 1, 5, 10, 50 and 100 ppm to the basal medium, as well as a control medium with no added samples, were prepared.

4. Antimicrobial activity test

The above-mentioned pre-incubation solution was inoculated into the above-mentioned test media and the control medium at a concentration of 1%, cultured under aerobic conditions for 16 hours at 35° C., the turbidities of the culture media were measured using the above-mentioned method and the rate of inhibition of *E. coli* proliferation was calculated according to the following formula.

Rate of inhibition of proliferation $(\%) = 100(1 - A/B)$ wherein A is the difference in turbidity of the test culture medium (the difference between the turbidity of the test culture medium after 16 hours of culture and the turbidity of the test culture medium before the culturing) and B is the turbidity of the control medium (the difference between the turbidity of the control culture medium after 16 hours of culture and the turbidity of the control culture medium before the culturing). The percentages of the rate of inhibition of proliferation are not in weight (same hereinafter).

(2) Sample preparation and results

A transparent supernatant of pepsin hydrolysate of bovine LF which was prepared according to the same method as in Example 1 was diluted to about 2% (W/V) with purified water, 100 μl were subjected to chromatography at a flow rate of 0.8 ml/min., using TSK gel ODS-120 T (manufactured by Tosoh Co., 4.6×150 mm) which had previously been equilibrated with a 20% acetonitrile solution containing 0.05% trifluoroacetic acid (TFA), and after ten minutes, elution in a linear gradient of 20 to 60% acetonitrile containing 0.05% TFA was performed for 30 minutes, the eluate was collected every minute starting five minutes after the LF hydrolysate was injected and the elution curve shown in FIG. 1 was obtained. FIG. 1 is the light absorption curve at 280 nm of the fractions eluted in linear gradient high-performance liquid chromatography, the horizontal axis denotes time (minutes), the right vertical axis the acetonitrile concentration and the dashed line shows the change in acetonitrile concentration. This process was repeated ten times and each fraction was vacuum-dried. The antimicrobial properties of each of the fractions was studied according to the above-mentioned experimental method, and the results confirmed an antimicrobial effect only of the fraction obtained after 24 to 25 minutes of eluate collection at a concentration of 5 ppm.

Figure 2:
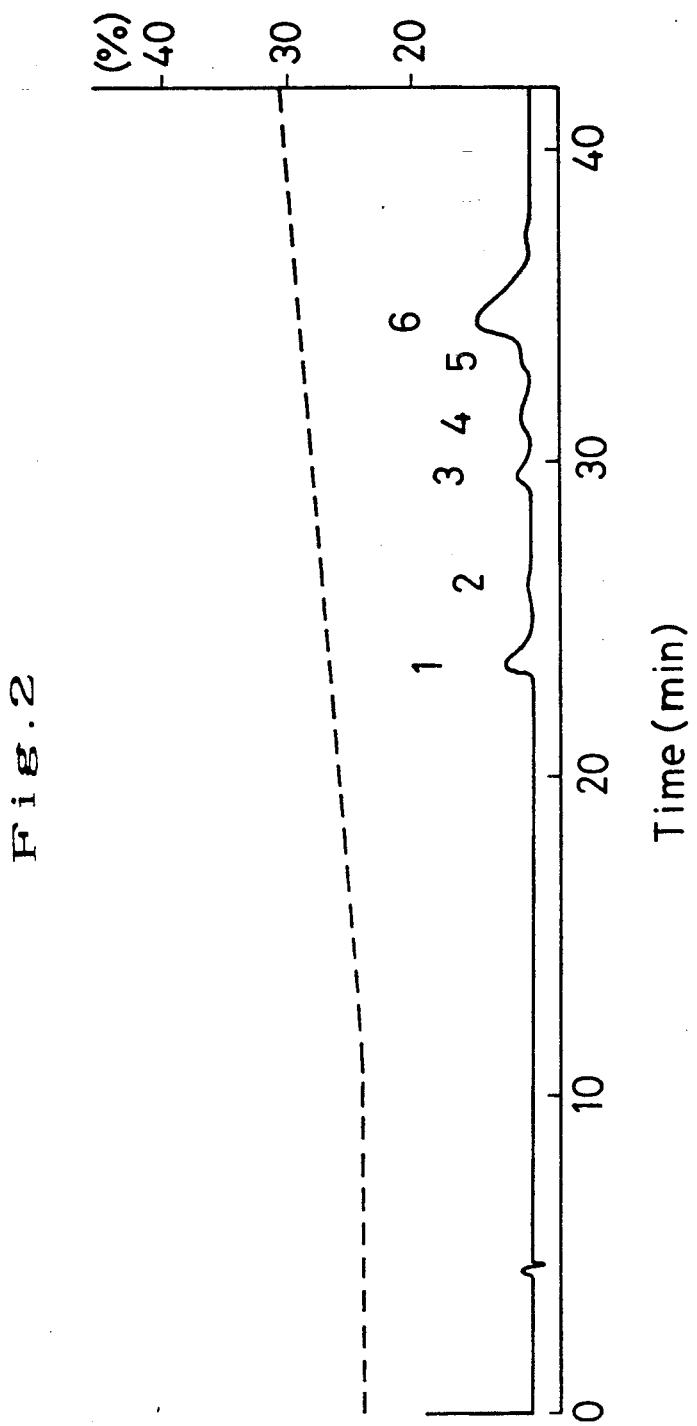

Next, this fraction was dissolved at 2% (W/V) in purified water, 100 μl of the solution were subjected to chromatography at a flow rate of 0.8 ml/min, using TSK gel ODS-120 T (manufactured by Tosoh Co., 4.6×150 mm) which had previously been equilibrated with a 20% acetonitrile solution containing 0.05% trifluoroacetic acid (TFA), and after ten minutes, elution in a linear gradient of 24 to 32% acetonitrile containing 0.05% TFA was performed for 30 minutes, six fractions were collected and the elution curve shown in FIG. 2 was obtained. FIG. 2 is the light absorption curve at 280 nm of the fractions eluted in linear gradient high-performance liquid chromatography, the horizontal axis denotes time (minutes), the right vertical axis the acetonitrile concentration, the dashed line shows the change in acetonitrile concentration and the numbers 1 to 6 appearing within the figure represent the numbers of the peaks. This process was repeated ten times, each fraction was vacuum-dried and the antimicrobial properties of each of the fractions was studied according to the above-mentioned experimental method. The results confirmed an antimicrobial effect only of peak 6, as shown in Table 1, at a concentration of 5 ppm. Since the yield of peaks 2, 4 and 5 was low, experiments involving addition of 100 ppm were not performed with regards to these peaks.

EXPERIMENT 2

This experiment was performed in order to determine the amino acid sequence of the antimicrobial peptide isolated in Experiment 1.

The peptide obtained in Experiment 1 was hydrolyzed by 6N hydrochloric acid and the amino acid composition was analyzed by conventional methods, using an amino acid analyzer. 25 cycles of Edman's degradation were performed on the same sample, using a gas-phase sequencer (manufactured by Applied Biosystems Co.), and a sequence of 25 amino acid residues was determined. In addition, the existence of a disulfide bond was confirmed using a disulfide bond analysis method (Analytical Biochemistry, Vol. 67, p. 493, 1975) in which DTNB (5,5-dithio-bis-(2-nitrobenzoic acid)) was used.

As a result it was determined that this peptide consisted of 25 amino acid residues, that the third and the 20th cysteine residues formed a disulfide bond, that to the third cysteine residue there were two amino acid residues bound on the N-terminal side, that to the 20th cysteine residue there were five amino acid residues bound on the C-terminal, respectively, forming the following amino acid sequence.

Two peptides were isolated from a hydrolysate of bovine LF using the same method as in Example 2.

(2) Experimental methods
The same method as in Experiment 1 was used.
(3) Results The results of this experiment are shown in Table 2. An antimicrobial effect was confirmed only in the two peptides which were analyzed using the same method as in Example 2 (peptide 1 eluted after 21 to 22 minutes and pepdde 2 eluted after 29 to 30 minutes of chromatography) at a concentration of 5 ppm.

EXPERIMENT 4

This experiment was performed in order to determine the amino acid sequence of the antimicrobial peptides isolated in Experiment 3.

The antimicrobial peptides isolated using the same method as in Experiment 3 were studied using the same method as in Experiment 2 and the following amino acid sequences of the two peptides were determined.

As a result it was determined that one of the peptides consisted of 38 amino acid residues, that the 16th and the 33rd cysteine residues formed a disulfide bond, that to the 16th cysteine residue there were 15 amino acid residues bound on the N-terminal side, that to the 33rd cysteine residue there were five amino acid residues bound on the C-terminal side, respectively.

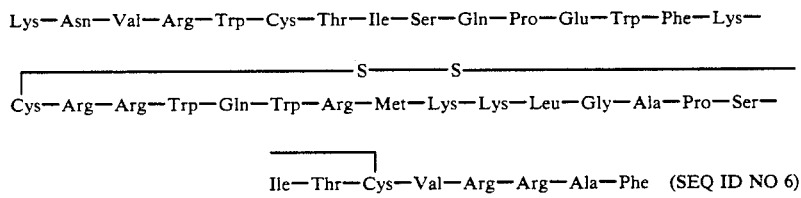

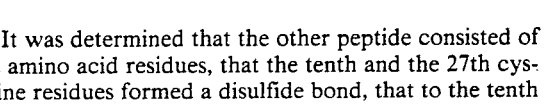

It was determined that the other peptide consisted of 32 amino acid residues, that the tenth and the 27th cysteine residues formed a disulfide bond, that to the tenth cysteine residue there were 9 amino acid residues bond on the N-terminal side, and that to the 27th cysteine residue there were five amino acid residues bound on the C-terminal side, respectively.

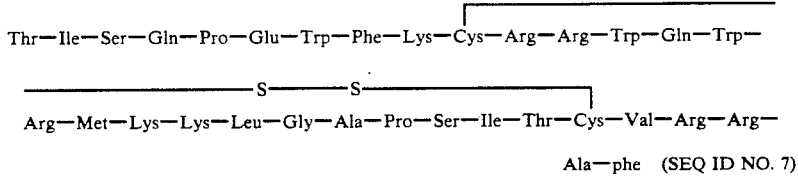

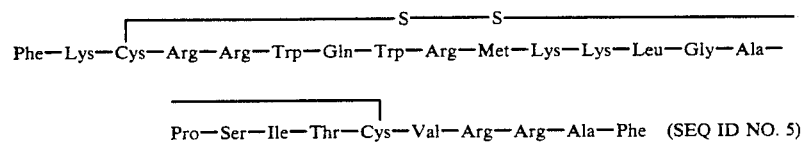

EXPERIMENT 3

This experiment was performed in order to study the antimicrobial activity of the antimicrobial peptides isolated from an acid hydrolysate of bovine LF.

(1) Sample preparation

EXPERIMENT 5

This experiment was performed in order to study the antimicrobial activity of the antimicrobial peptide isolated from a pepsin hydrolysate of human LF.

(1) Sample preparation

A peptide was isolated from a hydrolysate of human LF by the same method sa in Example 3.

(2) Experimental methods

The same method as in Experiment 1 was used.

(3) Results

An antimicrobial effect was confirmed only in the peptide which was isolated using the same method as in Example 3, and the rates of inhibition of proliferation when this peptide was added at concentrations of 1, 5, 10, 50 and 100 ppm were 3, 86, 100, 100 and 100%, respectively.

EXPERIMENT 6

This experiment was performed in order to determine the amino acid sequence of the antimicrobial peptide isolated in Experiment 5.

The antimicrobial peptide isolated using the same method as in Experiment 5 was studied using the same method as in Experiment 2 and the following amino acid sequence was determined.

As a result it was determined that this peptide consisted of 47 amino acid residues, that the ninth and the 26th cysteine residues formed a disulfide bond, that to the ninth cysteine residues there were eight amino acid residues bound on the N-terminal side, that ten amino acid residues were bound on the C-terminal side and that the 35th cysteine residue on the C-terminal side formed a disulfide bond with a cysteine residue contained in 11 amino acid residues.

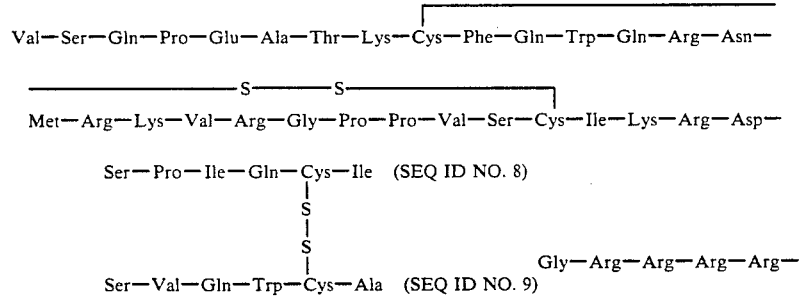

EXPERIMENT 7

This experiment was performed in order to study the antimicrobial activity of an antimicrobial peptide isolated from a V8 protease hydrolysate of human LF.

(1) Sample preparation

A peptide was isolated from a hydrolysate of human LF using the same method as in Example 4.

(2) Experimental methods

The same method as in Experiment 1 was used.

(3) Results

An antimicrobial effect was confirmed only in the peptide which was isolated using the same method as in Example 4, and the rates of inhibition of proliferations when this peptide was added at concentrations of 1, 5, 10, 50 and 100 ppm were 7, 93, 100 and 100%, respectively.

EXPERIMENT 8

This experiment was performed in order to determine the amino acid sequence of the antimicrobial peptide isolated in Experiment 7.

The antimicrobial peptide isolated using the same method as in Experiment 7 was studied using the same method as in Experiment 2 and the following amino acid sequence was determined.

As a result it was determined that this peptide consisted of 25 amino acid residues, that the fourth and the 21st cysteine residues formed a disulfide bond, that to the forth cysteine residue there were three amino acid residues bound on the N-terminal side and that to the 21st cysteine residue there were four amino acid residues bound on the C-terminal side, respectively.

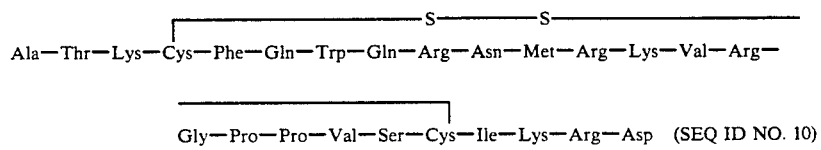

EXPERIMENT 9

This experiment was performed in order to study the antimicrobial activity of a chemically synthesize peptide which was identical to the peptide whose amino acid sequence was determined in Experiment 2.

(1) Sample preparation

A peptide was synthesized using the same method as in Example 5

(2) Experimental methods

The same method as in Experiment 1 was used.

(3) Results

The results of this experiment showed that the chemically-synthesized peptide exhibited antimicrobial properties equivalent to the antimicrobial properties of the peptide which was isolated from bovine LF hydrolysate in Experiment 2.

EXPERIMENT 10

The experiment was performed in order to study the antimicrobial properties of the acetoamidomethylated peptide which was produced in the process of peptide synthesis in Experiment 9.

An acetoamidomethylated peptide was synthesized using the same method as in Example 5 and studied using the same method as in Experiment 1, the results of which showed an antimicrobial effect of the acetoamidomethylated peptide at a concentration of 5 ppm.

EXPERIMENT 11

This experiment was performed in order to study the antimicrobial properties of a peptide whose disulfide bonds were cleaved.

The peptide prepared using the same method as in Experiment 1 was reduced and subjected to pyridylethylation according the method of Fulmar et al (Analytical Biochemistry, Vol. 142, p. 336, 1984). The peptide was studied using the same method as in Experiment 1, and, as a result, antimicrobial actibity was seen at a concentration of 5 ppm.

EXPERIMENT 12

This experiment was performed in order to study the antimicrobial spectrum of the antimicrobial peptides of the present invention.

(1) Sample preparation

An antimicrobial peptide was prepared using the same method as in Example 1 and sterilized by filtration using a 0.45 μm Millex filter prior to use.

(2) Experimental methods

The various microorganisms shown in Table 3 and in Table 4 were incubated for 16 to 20 hours in 2 ml of peptone medium which consisted of 1% Bactopeptone (manufactured by Difco Laboratory Co.), or in 2 ml of PYG medium which consisted of 1% Bactopeptone (manufactured by Difco Laboratory Co.), 1% glucose and 0.05% yeast extract. The antimicrobial peptide was added to each medium at various ratios of 0 μg/ml to 60 μg/ml. Standard bacterial strains of various microorganisms in the logarithmic phase were inoculated into the various media at a cell concentration of $10^6$/ml and incubated at 37° C., with the exception of the bacterial strains mentioned in the footnotes of the tables. The growth of the various microorganisms was studied by measuring the light absorption at 660 nm. The minimum concentration of the antimicrobial peptide which completely inhibited growth of the various microorganisms was considered the minimum inhibitory concentration (MIC. μg/ml).

(3) Results

The results of this experiment are shown in Table 3 and Table 4. As is clear from Table 3 and Table 4, the antimicrobial peptide showed an antimicrobial activity at low concentrations of less than 45 μg/ml against many types of gram-positive bacteria and gram-negative bacteria, including aerobic and anaerobic bacteria and yeast. The concentration of the antimicrobial peptide in which growth of the microorganisms was completely inhibited varied depending on the medium. Among the microorganisms studied, *Pseudomonas fluorescens* IFO-141602 and *Enterococcus faecalis* ATCC-E19433 showed resistance to the antimicrobial peptide under the conditions of this experiment.

In addition, virtually identical results were obtained with other antimicrobial peptides of the present invention.

EXPERIMENT 13

This experiment was performed in order to study the effect of the antimicrobial peptides of the present invention on the survival of various microorganisms.

(1) Sample preparation

An antimicrobial peptide was prepared using the same method as in Example 1.

(2) Experimental methods

The various microorganisms shown in Table 5 and Table 6 in the logarithmic phase were suspended in a PYG medium identical to that used in Experiment 12 and a sample to which the antimicrobial peptide was added at a ratio of 31 μg/ml, as well as a control to which the antimicrobial peptide was not added, were incubated using a shaking incubator with the water bath maintaining a temperature of 30° C. After 60 minutes, culture media were prepared by diluting ten-fold with a peptone medium identical to the one used in Experiment 12, the bacterial count was measured using an agar plate or other media suitable for measurement of the colonies formed, and the survival rates of the various microorganisms were studied by calculating the percentages of the antimicrobial peptide-added samples with respect to the control.

(3) Results

The results of this experiment are shown in Table 5 and Table 6. As is clear from Table 5 and Table 6, the antimicrobial peptide showed an antimicrobial activity against many types of gram-positive bacteria and gram-negative bacteria including aerobic and anaerobic bacteria and yeast.

The antimicrobial properties of the antimicrobial peptide were demonstrated by a complete loss of colony formation capacity of the microorganisms at a concentration of 31 μg/ml within 60 minutes. Among the microorganisms studied, *Pseudomonas fluorescens* IFO-141602 and *Bifidobacterium bifidum* ATCC-15695 showed resistance to the antimicrobial peptide under the conditions of this experiment.

In addition, virtually identical results were obtained with other antimicrobial peptides of the present invention.

EXPERIMENT 14

This experiment was performed in order to study the effect of the antimicrobial peptide of the present invention against fungus.

(1) Sample preparation

An antimicrobial peptide was prepared using the same method as in Example 1 and sterilized by filtration using a 0.45 μm Millex filter prior to use.

(2) Experimental methods

The fungi shown in Table 7 were inoculated into 4 ml of Sabouraud's slant medium which consisted of 1% Bactopeptone (manufactured by Difco Laboratory Co.), 4% glucose and 1.5% agar, and incubated for one week at 25° C. 1 ml of 1% peptone water was layered on top of the medium, agitated with a Vortex and the spores were collected. 20 μl of the spore suspension solution were incubated for 20 hours in 2 ml of peptone medium which consisted of 1% Bactopeptone (manufactured by Difco Laboratory Co.) or in 2 ml of PYG medium which consisted of 1% Bactopeptone (manufactured by Difco Laboratory Co.), 1% glucose and 0.05% yeast extract. The antimicrobial peptide was added to each medium at various ratios ranging from 0 μg/ml to 60 μg/ml. The initial fungus count was measured in a Sabouraud agar medium to which 0.005% of Rose bengal was added, and the concentration at which no growth of hyphae was seen after 20 hours was considered the minimum inhibitory concentration (MIC. μg/ml).

(3) Results

The results of this experiment are shown in Table 7. As is clear from Table 7, the antimicrobial peptide showed an antimicrobial activity at low concentrations of less than 45 μg/ml against various fungi. Overall, the concentration of the antimicrobial peptide at which growth of fungi was completely inhibited varied depending on the medium. Among the fungi studied, Aspergillus fumigatus JCM-1739 and Rhizopus oryzae JCM-5557 showed resistance to the antimicrobial peptide under the conditions of this experiment. In addition, virtally identical results were obtained with other antimicrobial peptides of the present invention.

EXPERIMENT 15

An antimicrobial peptide which was produced using the same method as in Example 1 was dissolved at a concentration of 0.001% in purified water, a tissue paper was immersed in the solution and a wet tissue paper (sample), usable as a towelette, was produced. A wet tissue paper, usable as a towelette, which was produced in the same way by immersing a tissue paper in purified water, was used as control.

0.3 ml of aqueous solution which contained $E.\ coli$ strain O-111 at a cell concentration of $10^6$/ml was placed in a sterilized plate and air-dried. The plate was wiped once with the sample or with the control, 5 ml of sterilized water was added to the plate and the surviving $E.\ coli$ bacteria in this sterilized water were incubated using a conventional method on a nutrient agar medium (Plate Count Agar; manufactured by Eiken Chemical Co.) and counted.

As a result, 42 $E.\ coli$ bacteria were counted from the plate which had been wiped with the sample, versus 38,000 $E.\ coli$ bacteria which were counted from the plate wiped with the control, and the wet tissue paper which was immersed in an aqueous solution of the antimicrobial peptide showed a remarkable bactericidal effect.

EFFECTS OF THE INVENTION

Since the antimicrobial peptide of the present invention possesses an antimicrobial activity which is considerably better than that of natural LF of LF hydrolysate and is effective against a wide range of microorganisms, it is suitable for a wide range of applications, and since it demonstrates an antimicrobial effect even in small amounts, it can be applied to food products etc. with hardly any effect of their flavor.

The present invention will now be explained in further detail by means of examples. Of course, the present invention is not limited to or by these examples.

EXAMPLE 1

50 mg of commercially available bovine LF (manufactured by Sigma Co.) was dissolved in 0.9 ml of purified water, the pH was adjusted to 2.5 with 0.1M hydrochloric acid, 1 mg of commercially available porcine pepsin (manufactured by Sigma Co.) was added and hydrolysis was performed for six hours at 37° C. Next, the pH was adjusted to 7.0 by adding 0.1N sodium hydroxide, the solution was heated to 80° C. for ten minutes and the enzyme was inactivated, the solution was cooled down to room temperature, centrifugation was performed at 15,000 rpm for 30 minutes and a transparent supernatant was obtained. 100 μl of this supernatant were subjected to high-performance liquid chromatography using TSK gel ODS-120 T (manufactured by Tosoh Co.) and at a flow rate of 0.8 ml/min., it was eluted for ten minutes after sample injection with 20% acetonitrile containing 0.05% TFA, after which elution in a gradient of 20 to 60% acetonitrile containing 0.05% TFA was performed for 30 minutes and the fraction eluted after 24 to 25 minutes was collected and vacuum-dried. The dried substance was dissolved at a concentration of 2% (W/V) in purified water, subjected again to high-performance liquid chromatography using TSK gel ODS-120 T (manufactured by Tosoh Co.), and at a flow rate of 0.8 ml/min., it was eluted for ten minutes after sample injection with 24% acetonitrile containing 0.05% TFA, after which elution in a gradient of 24 to 32% acetonitrile containing 0.05% TFA was performed for 30 minutes and the fraction eluted after 33.5 to 35.5 minutes was collected. The above-mentioned procedure was repeated 25 times and about 1.5 mg of vacuum-dried antimicrobial peptide was obtained.

EXAMPLE 2

50 mg of commercially available bovine LF (manufactured by the Belgium Oleofina Co.) was dissolved in 0.95 ml of purified water, the pH was adjusted to 2.0 with 1M hydrochloric acid, hydrolysis was performed for 15 minutes at 120° C. and the solution was cooled down to room temperature. Next, the pH was adjusted to 7.0 by adding 0.1N sodium hydroxide, centrifugation was performed at 15,000 rpm for 30 minutes and a transparent supernatant was obtained. 100 μl of this supernatant were subjected to high-performance liquid chromatography using TSK gel ODS-120 T (manufactured by Tosoh Co.) and at a flow rate of 0.8 ml/min., it was eluted for ten minutes after sample injection with 20% acetonitrile containing 0.05% TFA, after which elution in a gradient of 20 to 60% acetonitrile containing 0.05% TFA was performed for 30 minutes and the fraction eluted after 23 to 25 minutes was collected and vacuum-dried. The dried substance was dissolved at a concentration of 2% (W/V) in purified water, subjected again to high-performance liquid chromatography using TSK gel ODS-120 T (manufactured by Tosoh Co.), and at a flow rate of 0.8 ml/min., it was eluted for ten minutes after sample injection with 24% acetonitrile containing 0.05% TFA, after which elution in a gradient of 24 to 32% acetonitrile containing 0.05% TFA was performed for 30 minutes and the fractions eluted after 21 to 22. minutes and after 29 to 30 minutes were collected. The above-mentioned procedure was repeated 25 times and about 3 mg of vacuum-dried antimicrobial peptide were obtained.

EXAMPLE 3

20 mg of commercially available human LF (manufactured by Sigma Co.) was dissolved in 1.0 ml of purified water, the pH was adjusted to 2.5 with 0.1M hydrochloric acid, 0.5 mg of commercially available porcine pepsin (manufactured by Sigma Co.) was added and hydrolysis was performed for five hours at 37° C. Next, the pH was adjusted to 7.0 by adding 0.1N sodium hydroxide, the solution was heated to 80° C. for ten minutes and the enzyme was inactivated, the solution was cooled down to room temperature, centrifugation was performed at 15,000 rpm for 30 minutes and a transparent supernatant was obtained. 100 μl of this supernatant were subjected to high-performance liquid chromatography using TSK gel ODS-120 T (manufactured by Tosoh Co.) and at a flow rate of 0.8 ml/min., it was eluted for ten minutes after sample injection with 20% acetonitrile containing 0.05% TFA, after which elution in a gradient of 20 to 60% acetonitrile containing 0.05% TFA was performed for 30 minutes, the fraction eluted after 23 to 24 minutes was collected and vacuum-dried. The dried substance was dissolved at a concentration of 2% (W/V) in purified water, subjected again to high-performance liquid chromatography using TSK gel ODS-120 T (manufactured by Tosoh Co.), and at a flow rate of 0.8 ml/min., it was eluted for ten minutes after sample injection with 24% acetonitrile containing 0.05% TFA, after which elution in a gradient of 24 to 32% acetonitrile containing 0.05% TFA was performed for 30 minutes and the fraction eluted after 28 to 31 minutes was collected. The above-mentioned procedure was repeated ten times and about 1 mg of vacuum-dried antimicrobial peptide was obtained.

EXAMPLE 4

50 mg of commercially available human LF (manufactured by Sigma Co.) was dissolved in 0.95 ml of 10 mM phosphate buffer solution, 1.5 mg of commercially available V8 protease (manufactured by Boehringer-Mannheim Co.) was added and hydrolysis was performed for eight hours at 37° C. Next, the pH was adjusted to 7.0 by adding 0.1N sodium hydroxide, the solution was heated to 80° C. for ten minutes and the enzyme was inactivated, the solution was cooled down to room temperature, centrifugation was performed at 15,000 rpm for 30 minutes and a transparent supernatant was obtained. 100 μl of this supernatant were subjected to high-performance liquid chromatography using TSK gel ODS-120 T (manufactured by Tosoh Co.) and, after sample injection at a flow rate of 0.8 ml/min., it was eluted for ten minutes with 20% acetonitrile containing 0.05% TFA, after which elution in a gradient of 20 to 60% acetonitrile containing 0.05% TFA was performed for 30 minutes and the fraction eluted after 23 to 24 minutes was collected and vacuum-dried. The dried substance was dissolved at a concentration of 2% (W/V) in purified water, subjected again to high-performance liquid chromatography using TSK gel ODS-120 T (manufactured by Tosoh Co.) and at a flow rate of 0.8 ml/min., it was eluted for ten minutes after sample injection with 24% acetonitrile containing 0.05% TFA, after which elution in a gradient of 24 to 32% acetonitrile containing 0.05% TFA was performed for 30 minutes and the fraction eluted after 25.5 to 26.5 minutes was collected. The above-mentioned procedure was repeated 25 times and about 3 mg of vacuum-dried antimicrobial peptide were obtained.

EXAMPLE 5

The peptide whose amino acid sequence was determined in Experiment 2 was synthesized using an automated peptide synthesizer (manufactured by Pharmacia LKB Biotechnology Co., Trademark. LKB Biolynk 4170). 390 mg of Fmoc-phenylalanine anhydride were fixed to Ultrosyn A resin (manufactured by Pharmacia LKB Biotechnology Co.) through the carboxyl group, using dimethylaminopyridine as a catalyst. Next, the resin was washed with dimethylformamide containing piperidine, and the protecting group of the amine functional group of the C-terminal amino acid was removed. 156 mg of the Fmoc-alanine anhydride of the second amino acid residue from the C-terminal were then coupled to the unprotected amine functional group of the above-mentioned phenylalanine residue. Subsequently the successive desired amino acids were fixed in the same manner, except for cysteine, in which an acetoamidomethylated Fmoc-amino acid was used, coupling of a phenylalanine residue which was 25th from the C-terminal was completed and a peptide chain of the desired amino acid sequence was formed. Next, the protective groups were removed and the peptide was released with a solvent (composed of 94% trifluoroacetic acid, 5% phenol and 1% ethandiol), the peptide was purified by using high-performance liquid chromatography, vacuum-dried and about 150 mg of acetoamidomethylated peptide were obtained. These 150 mg of acetoamidomethylated peptide were dissolved in 10 ml of 90% acetic acid aqueous solution, 2.5 ml of 1M hydrochloric acid were added, furthermore 100 ml of 50 mM iodine dissolved in a 90% acetic acid aqueous solution were added, the solution was vigorously stirred for 30 minutes, 5 ml of 1M sodium thiosulfate aqueous solution were added and the reaction was stopped, and the solution was concentrated to about 40 ml with a rotary evaporator. This concentrated solution was purified by using a Sephadex G 15 (manufactured by Pharmacia Co.) column (50×500 mm), vacuum-dried, and about 70 mg of antimicrobial peptide were obtained.

EXAMPLE 6

1 mg of the antimicrobial peptide obtained using the same method as in Example 1 was dissolved in a mixture of 0.5 g of methylcellulose and 100 ml of purified water, and an antimicrobial agent was producted.

EXAMPLE 7

5 mg of the antimicrobial peptide obtained using the same method as in Example 4 were dissolved in a mixture of 20 ml of ethyl alcohol and 80 ml of purified water, and an antimicrobial agent was produced.

EXAMPLE 8

An eye drop of the following composition was produced.

| Boric acid | 1.9(%) |
|---|---|
| The antimicrobial peptide of Example 1 | 0.2 |
| Methylcellulose | 0.5 |

EXAMPLE 9

A mouth wash with the following composition was produced. This mouth wash is 50 to 10 times diluted with water at the time of use.

| Ethyl alcohol | 20.0(%) |
|---|---|
| Saccharin sodium | 3.0 |
| The antimicrobial peptide of Example 2 | 1.0 |
| Purified water | 76.0 |

EXAMPLE 10

A chewing gum with the following composition was produced.

| Gum base | 25.00(%) |
|---|---|
| Calcium carbonate | 2.00 |
| Flavoring | 1.00 |
| The antimicrobial peptide Example 3 | 0.03 |
| Sorbitol powder | 71.97 |

EXAMPLE 11

An antiperspirant spray with the following composition was produced.

| | |
|---|---|
| 1-Menthol | 2.0(%) |
| Propylene glycol | 0.4 |
| Ethyl alcohol | 3.5 |
| Freon 11 (trademark; manufactured by du Pont Co.; trichlorofluoromethane) | 30.0 |
| Freon 12 (trademark; manufactured by due Pont Co.; dichlorodifluoromethane) | 48.0 |
| Diethyl ether | 16.0 |
| The antimicrobial peptide of Example 5 | 0.1 |

EXAMPLE 12

A toothpaste with the following composition was produced.

| | |
|---|---|
| Sorbitol | 47.0(%) |
| Glycerine | 15.0 |
| Carboxymethyl cellulose/sodium | 2.0 |
| Sorbitan fatty acid ester | 1.0 |
| Saccharin sodium | 1.0 |
| The antimicrobial peptide of Example 1 | 0.1 |

EXAMPLE 13

A skin wash with the following composition was produced. This skin wash is 50 times diluted with water at the time of use.

| | |
|---|---|
| Sodium chloride | 8.0% |
| The antimicrobial peptide of Example 2 | 1.0 |
| Purified water | 91.0 |

EXAMPLE 14

An antifungal agent with the following composition was produced.

| | |
|---|---|
| Ethyl alcohol | 20.00(%) |
| The antimicrobial peptide of Example 5 | 0.01 |
| Purified water | 79.99 |

EXAMPLE 15

A cut flower preservative with the following composition was produce. This cut flower preservative is 100 times diluted with water at the time of use.

| | |
|---|---|
| Avicel (Microcrystalline form of cellulose) | 90.0(%) |
| Table salt | 9.0 |
| The antimicrobial peptide of Example 1 | 1.0 |

TABLE 1

| Sample | Added quantity (ppm) and inhibitory rate (%) | | | | |
|---|---|---|---|---|---|
| | 1 | 5 | 10 | 50 | 100 |
| peak 1 | 0 | 0 | 0 | 0 | 0 |
| Peak 2 | 0 | 0 | 0 | 0 | — |
| Peak 3 | 0 | 0 | 0 | 0 | 0 |
| Peak 4 | 0 | 0 | 0 | 0 | — |
| Peak 5 | 0 | 0 | 0 | 0 | 2 |
| Peak 6 | 6 | 100 | 100 | 100 | 100 |

TABLE 2

| Sample | Added quantity (ppm) and inhibitory rate (%) | | | | |
|---|---|---|---|---|---|
| | 1 | 5 | 10 | 50 | 100 |
| Peptide 1 | 4 | 100 | 100 | 100 | 100 |
| Peptide 2 | 8 | 100 | 100 | 100 | 100 |

TABLE 3

| Gram-positive bacteria strain | Minimum Inhibitory Concentration (µg/ml) | |
|---|---|---|
| | Peptone medium | PYG medium |
| Corynebacterium ammoniagenes JCM-1306 *1 | 0.3 | 0.3 |
| Corynebacterium renale JCM-1322 *1 | 0.6 | 1 |
| Corynebacterium diphtheriae JCM-1310 | 6 | 18 |
| Listeria monocytogenes IDF-1b | 0.6 | 2 |
| Staphylococcus aureus JCM-2413 | 6 | 18 |
| Staphylococcus aureus JCM-2179 | 3 | 6 |
| Staphylococcus aureus JCM-2151 | 3 | 6 |
| Staphylococcus hominus JCM-2419T | 2 | 3 |
| Staphylococcus epidermidis JCM-2414T | 3 | 6 |
| Staphylococcus haemolyticus JCM-2416T | 0.6 | 1 |
| Clostridium perfringens ATCC-60 *2 | 12 | 24 |
| Clostridium paraputrificum MMI-25 *2 | NG | 3 |
| Bacillus subtilis ATCC-6633 | 0.6 | 2 |
| Bacillus natto IFO-3009 | 1 | 2 |
| Bacillus circulans JCM-2504T | 0.3 | 0.6 |
| Bacillus cereus MMI-272 | 9 | 9 |
| Enterococcus faecalis ATCC-E19433 | >60 | >60 |
| Lactobacillus casei MMI-114 *1 | NG | 12 |
| Streptococcus thermophilus ATCC-19258 | NG | 3 |
| Streptococcus lactis ATCC-19435 | NG | 3 |
| Streptococcus bovis JCM-5672 | 2 | 6 |
| Streptococcus cremoris ATCC-9265 *1 | NG | 3 |
| Streptococcus mutans JCM-5705T | 2 | 6 |
| Streptococcus mutans JCM-5175 | NG | 6 |
| Streptococcus mutans JCM-5176 | NG | 3 |

(Notes)
1) Indications of bacteria strain source
IID: The Medical School Laboratories of Tokyo University
MMI: Storage at the Laboratories of the Applicant
JCM: Physicochemical Laboratories
IFO: Fermentation Laboratories of Osaka University
IDF: Japanese International Dairy Federation
ATCC: American Type Culture Collection
2) *1: Culture at 30° C.
*2: Anaerobic bacteria strain, cultured at an enviroment of 85% nitrogen, 10% carbon dioxide, 5% hydrogen
3) NG indicates no growth in this medium

TABLE 4

| Microorganism | Minimum Inhibitory Concentration (μg/ml) | |
|---|---|---|
| | Peptone medium | PYG medium |
| Gram-negative bacterial strain | | |
| *Escherichia coli* IID-861 | 6 | 9 |
| *Escherichia coli* MMI-0111 | 6 | 12 |
| *Salmonella enteriditis* IID-604 | 12 | 18 |
| *Yersinia enterocolitica* IID-981 | 6 | 24 |
| *Proteus vulgaris* JCM-1668T | 12 | 45 |
| *Klebsiella pneumoniae* JCM-1662T *1 | 6 | 12 |
| *Pseudomonas aeruginosa* MMI-603 | 12 | 24 |
| *Pseudomonas aeruginosa* IFO-3445 | 6 | 18 |
| *Pseudomonas aeruginosa* IFO-3446 | 9 | 24 |
| *Pseudomonas aeruginosa* IFO-3448 | 9 | 45 |
| *Pseudomonas aeruginosa* IFO-3452 | 6 | 30 |
| *Pseudomonas fluorescens* IFO-141602 *1 | >60 | >60 |
| Yeast | | |
| *Candida albicans* JCM-2900 *1 | 18 | 24 |
| *Candida albicans* JCM-1542T *1 | 18 | 24 |

(Notes) Same notes as in Table 3

TABLE 5

| Gram-positive bacteria strain | Live bacteria count in 1 ml after 60 min. | | Survival rate (%) |
|---|---|---|---|
| | Control | Antimicrobial peptide | |
| *Bacillus subtilis* ATCC-6633 | $2.8 \times 10^5$ | <100 | <0.04 |
| *Bacillus natto* IFO-3009 | $4.5 \times 10^5$ | <100 | <0.02 |
| *Bacillus circulans* JCM-2504T | $8.3 \times 10^5$ | <100 | <0.01 |
| *Bacillus careus* MMI-272 | $3.5 \times 10^4$ | 520 | 1.4 |
| *Enterococcus faecalis* ATCC-E19433 | $2.0 \times 10^6$ | $1.1 \times 10^6$ | 55 |
| *Streptococcus thermophilus* ATCC-19258 | $1.7 \times 10^4$ | <100 | <0.59 |
| *Streptococcus lactis* ATCC-19435 | $2.4 \times 10^5$ | 100 | 0.04 |
| *Streptococcus bovis* JCM-5672 | $5.2 \times 10^5$ | $1.8 \times 10^4$ | 3.5 |
| *Streptococcus mutans* JCM-5705T | $3.2 \times 10^6$ | 1300 | 0.04 |
| *Streptococcus mutans* JCM-5175 | $3.0 \times 10^4$ | <100 | <0.33 |
| *Streptococcus mutans* JCM-5176 | $7.0 \times 10^4$ | 7600 | 11 |
| *Corynebacterium ammoniagenes* JCM-1306 | $2.8 \times 10^5$ | <100 | <0.04 |
| *Corynebacterium renale* JCM-1322 | $6.4 \times 10^5$ | <100 | <0.02 |
| *Corynebacterium diphtheriae* JCM-1310 | $2.0 \times 10^4$ | 400 | 2.0 |
| *Staphylococcus aureus* JCM-2413 | $2.4 \times 10^6$ | $9.0 \times 10^5$ | 38 |
| *Staphylococcus aureus* JCM-2179 | $9.1 \times 10^5$ | <100 | <0.01 |
| *Staphylococcus aureus* JCM-2151 | $2.1 \times 10^6$ | 1700 | 0.8 |
| *Staphylococcus hominus* JCM-2419T | $8.8 \times 10^5$ | $7.7 \times 10^5$ | 88 |
| *Staphylococcus epidermidis* JCM-2414T | $8.0 \times 10^5$ | 3900 | 0.5 |
| *Staphylococcus haemolyticus* JCM-2416T | $1.4 \times 10^5$ | <100 | <0.07 |
| *Clostridium perfringens* ATCC-6013 *1 | $1.2 \times 10^5$ | 1000 | 0.08 |
| *Bifidobacterium bifidum* ATCC-15696 *1 | $5.0 \times 10^4$ | $5.7 \times 10^4$ | 100 |
| *Bifidobacterium adolescens* ATCC-15703 *1 | $2.0 \times 10^5$ | $6.3 \times 10^4$ | 32 |
| *Bifidobacterium breve* ATCC-15700 *1 | $4.0 \times 10^5$ | $4.6 \times 10^4$ | 12 |
| *Bifidobacterium longum* ATCC-15707 *1 | $4.8 \times 10^5$ | $3.1 \times 10^4$ | 7 |

TABLE 5-continued

| Gram-positive bacteria strain | Live bacteria count in 1 ml after 60 min. | | Survival rate (%) |
|---|---|---|---|
| | Control | Antimicrobial peptide | |
| *Bifidobacterium infantis* ATCC-15697 *1 | $2.0 \times 10^4$ | <100 | <0.05 |

(Notes)
1) Indications of bacteria strain source are the same as in Table 3.
2) *1 Anaerobic bacteria strain, cultured at an environment of 85% nitrogen, 10% carbon dioxide, 5% hydrogen, at 37° C.
*2 Microaerophilic bacterial strain, cultured by using Campypak gas system (manufactured by BRL Laboratory Co.), at 37° C.
3) Antimicrobial peptide concentration: 31 μg/ml

TABLE 6

| Microorganism | Live bacteria count in 1 ml after 60 min. | | Survival rate (%) |
|---|---|---|---|
| | Control | Antimicrobial peptide | |
| Gram-negative bacteria strain | | | |
| *Escherichia coli* IID-861 | $1.2 \times 10^5$ | <100 | <0.08 |
| *Escherichia coli* MMI-0111 | $4.3 \times 10^6$ | <100 | <0.01 |
| *Salmonella enteriditis* IID-604 | $5.2 \times 10^5$ | $1.8 \times 10^4$ | 3.5 |
| *Proteus vulgaris* JCM-1668T | $5.2 \times 10^6$ | $1.6 \times 10^6$ | 31 |
| *Klebsiella pneumoniae* JCM-1662T | $3.2 \times 10^6$ | <100 | <0.01 |
| *Pseudomonas aeruginosa* MMI-603 | $3.4 \times 10^6$ | 3900 | 0.1 |
| *Pseudomonas aeruginosa* IFO-3445 | $1.0 \times 10^6$ | 1100 | 0.1 |
| *Pseudomonas aeruginosa* IFO-3446 | $2.6 \times 10^5$ | <100 | <0.04 |
| *Pseudomonas aeruginosa* IFO-3448 | $4.2 \times 10^5$ | 3900 | 0.9 |
| *Pseudomonas aeruginosa* IFO-3452 | $2.6 \times 10^5$ | 100 | 0.04 |
| *Pseudomonas fluorescens* IFO-14160 | $3.1 \times 10^6$ | $3.4 \times 10^6$ | 100 |
| *Bacteroides distasonis* MMI-M602 *1 | $3.0 \times 10^5$ | 3400 | 1.1 |
| *Bacteroides vulgatus* MMI-S601 *1 | $6.0 \times 10^5$ | 500 | 0.1 |
| *Campylobacter jejuni* JCM-2013 *2 | $3.1 \times 10^6$ | 2800 | 0.1 |
| Yeast | | | |
| *Candida albicans* JCM-2900 | $6.7 \times 10^5$ | 2100 | 0.3 |
| *Candida albicans* JCM-1542T | $5.8 \times 10^5$ | 2300 | 0.4 |

(Notes) Same notes as in Table 5

TABLE 7

| Fungus strain | Initial fungus count | Minimum Inhibitory Concentration (μg/ml) | |
|---|---|---|---|
| | | Peptone medium | PYG medium |
| *Aspergillus fumigalus* JCM1739 | $1.1 \times 10^5$ | >60 | >60 |
| *Aspergillus niger* JCM5546 | $4.4 \times 10^5$ | 30 | >60 |
| *Penicillium pinophilum* JCM5593 | $1.5 \times 10^3$ | 3 | 45 |
| *Penicillium vermiculatum* JCM5594 | $1.4 \times 10^3$ | 6 | 45 |
| *Nannizzia incurvala* JCM1906 | $8.0 \times 10^3$ | 3 | 9 |

TABLE 7-continued

| Fungus strain | Initial fungus count | Minimum Inhibitory Concentration (μg/ml) | |
|---|---|---|---|
| | | Peptone medium | PYG medium |
| Sporothrix cyanescens JCM2114 | $1.2 \times 10^5$ | 9 | 18 |
| Rhizopus oryzae JCM5557 | $7.1 \times 10^3$ | >60 | >60 |

(Notes)
JCM: Physicochemical Laboratories

---

We claim:

1. A substantially purified and isolated peptide having antimicrobial activity which consists of an amino acid sequence selected from the group consisting of SEQ ID NO. 1 and 2.

2. A substantially purified and isolated peptide having antimicrobial activity which consists of an amino acid sequence selected from the group consisting of SEQ ID NO. 3 and 4.

3. A substantially purified and isolated peptide having antimicrobial activity which consists of an amino acid sequence selected from the group consisting of SEQ ID NO. 5, 6, 7, 8, 9 and 10.

4. A substantially purified and isolated antimicrobial peptide consisting of 25 to 38 amino acid residues including an amino acid sequence selected from the group consisting of SEQ ID NO. 1 and 2.

5. A substantially purified and isolated antimicrobial peptide consisting of 25 to 47 amino acid residues including an amino acid sequence selected from the group consisting of SEQ ID NO. 3 and 4.

6. An antimicrobial composition which comprises at least one antimicrobial peptide according to claim 4 or claim 5, a pharmaceutically or sitologically accepted salt thereof, or a mixture thereof.

7. The antimicrobial composition according to claim 6, wherein the at least one antimicrobial peptide, salt or mixture is contained in a concentration of at least 5 ppm by weight.

* * * * *